United States Patent
Lacey (10) Patent No.: US 7,338,208 B2
(45) Date of Patent: Mar. 4, 2008

(54) METHODS AND APPARATUS FOR CT SYSTEM THERMAL CONTROL ARCHITECTURE

(75) Inventor: Joseph James Lacey, Cambridge, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/284,513

(22) Filed: Nov. 22, 2005

(65) Prior Publication Data

US 2006/0109956 A1    May 25, 2006

Related U.S. Application Data

(60) Provisional application No. 60/630,796, filed on Nov. 24, 2004.

(51) Int. Cl.
*H01J 35/10* (2006.01)
(52) U.S. Cl. .................................................... 378/199
(58) Field of Classification Search ............. 378/4–20, 378/199, 210; 165/59, 205, 208, 214, 244, 165/247
See application file for complete search history.

(56) References Cited

U.S. PATENT DOCUMENTS

| | | | | |
|---|---|---|---|---|
| 4,969,167 A | * | 11/1990 | Zupancic et al. ............ 378/19 |
| 5,444,752 A | * | 8/1995 | Dobbs et al. ................ 378/19 |
| 5,819,137 A | * | 10/1998 | Hoffman et al. ............. 399/93 |
| 6,104,003 A | * | 8/2000 | Jones ......................... 219/400 |
| 6,459,757 B1 | | 10/2002 | Lacey |
| 6,900,565 B2 | * | 5/2005 | Preston ........................ 310/88 |
| 6,909,775 B2 | * | 6/2005 | Ray et al. ................... 378/141 |
| 7,065,173 B2 | * | 6/2006 | Lacey et al. ................. 378/19 |
| 2002/0011097 A1 | * | 1/2002 | Kuderer et al. ............ 73/61.57 |
| 2004/0022351 A1 | * | 2/2004 | Lacey et al. ................. 378/19 |
| 2004/0071259 A1 | * | 4/2004 | Lacey et al. ................. 378/19 |
| 2004/0159713 A1 | * | 8/2004 | Schmidt et al. ............ 236/49.3 |
| 2004/0202287 A1 | * | 10/2004 | Muller ....................... 378/199 |
| 2004/0228450 A1 | * | 11/2004 | Mueller ..................... 378/199 |
| 2004/0240625 A1 | * | 12/2004 | Kendall ..................... 378/199 |

* cited by examiner

*Primary Examiner*—Edward J. Glick
*Assistant Examiner*—Anastasia S. Midkiff
(74) *Attorney, Agent, or Firm*—Armstrong Teasdale LLP (57) ABSTRACT

A method of cooling a medical imaging system that includes a gantry is provided. The method includes supplying air to the gantry. The supplied air is conditioned to reduce variation of the temperature within the gantry. After the air is conditioned it is channeled throughout the gantry to a plurality of heat producing electronic devices within the gantry.

20 Claims, 6 Drawing Sheets

METHODS AND APPARATUS FOR CT SYSTEM THERMAL CONTROL ARCHITECTURE

CROSS REFERENCE TO RELATED PATENTS

This application claims the benefit of U.S. provisional application No. 60/630,796 filed Nov. 24, 2004, which is herein incorporated in its entirety.

BACKGROUND OF THE INVENTION

This invention relates generally to methods and apparatus for computed tomography (CT), and more particularly to methods and apparatus that provide for thermal control in CT systems.

Air cooling of CT systems offers a good combination of simplicity and functionality when the factors of design time, cost and system sitting are considered. One problem with air cooling in a CT system is that there is a local temperature control solution for controlling the photodiode that is dependent and effected by the global system air temperature and flow control. Typical systems simply rely on controlling the bulk air temperature of the gantry (system) air temperature as measured at some convenient location in the gantry. One problem currently being addressed is that with CT system electronic power consumption on the rise it may be no longer feasible to have independent local and global temperature control systems. A further issue for air cooled systems with increased power consumption is to remove audible noise as more power consumption typically uses more and/or larger fans. Lastly, as more fans are added to a higher wattage CT system reliability concerns and field service to replace failed fans or clean air filters become larger more expensive long term problems.

BRIEF DESCRIPTION OF THE INVENTION

In one aspect, a method of cooling a medical imaging system that includes a gantry is provided. The method includes supplying air to the gantry. The supplied air is conditioned to reduce variation of the temperature within the gantry. After the air is conditioned it is channeled throughout the gantry to a plurality of heat producing electronic devices within the gantry.

In another aspect, a medical imaging system is provided. The medical imaging system includes a gantry having a controller configured to receive signals indicative of a plurality of temperatures within the gantry. A local thermal control system is further provided to maintain a predetermined temperature at a plurality of electronic devices within the gantry. Finally, a bulk thermal control system is provided to maintain a predetermined temperature within the gantry.

DETAILED DESCRIPTION OF THE INVENTION

There are herein provided thermal control methods and apparatus useful for imaging systems such as, for example, but not limited to a Computed Tomography (CT) System. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 1:
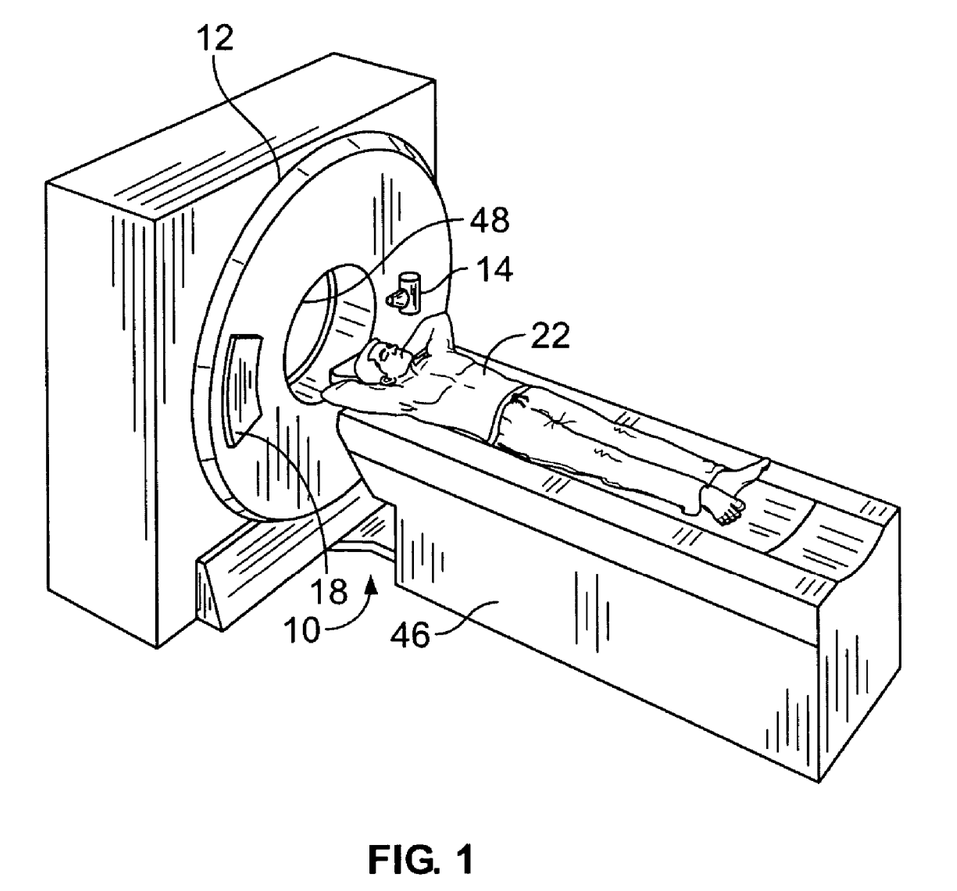
FIG. 1 is a pictorial view of a CT imaging system embodiment.
Figure 2:
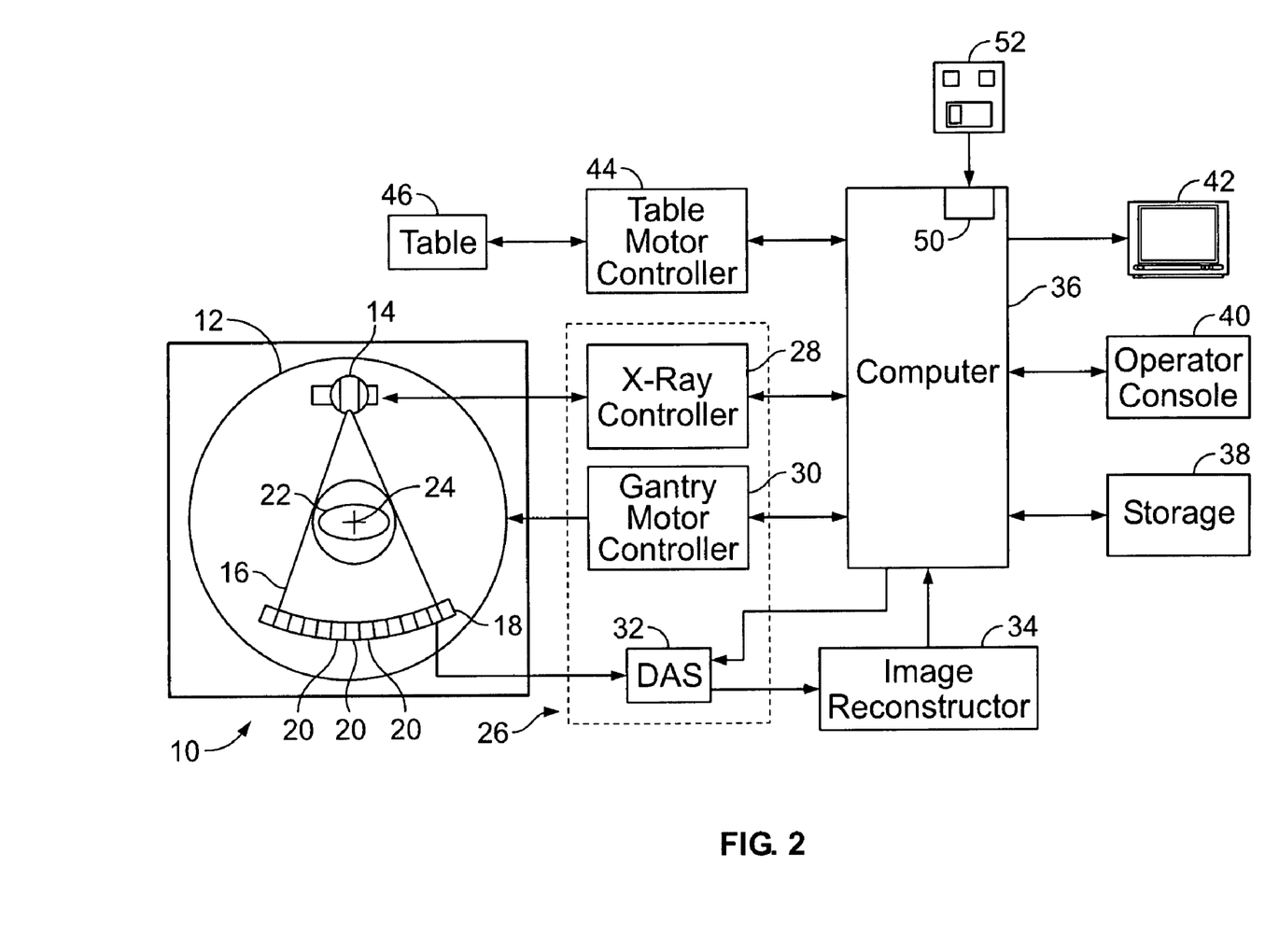
FIG. 2 is a block schematic diagram of the system illustrated in FIG. 1.

FIG. 1 is a pictorial view of a CT imaging system 10 in accordance with an embodiment of the present invention. FIG. 2 is a block schematic diagram of system 10 illustrated in FIG. 1. In the exemplary embodiment, a computed tomography (CT) imaging system 10 is shown as including a gantry 12 representative of a "third generation" CT imaging system. Gantry 12 has a radiation source 14 that projects a cone beam 16 of X-rays toward a detector array 18 on the opposite side of gantry 12.

Detector 0array 18 is formed by a plurality of detector rows (not shown in FIGS. 1 and 2) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via a console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center.

Figure 3:
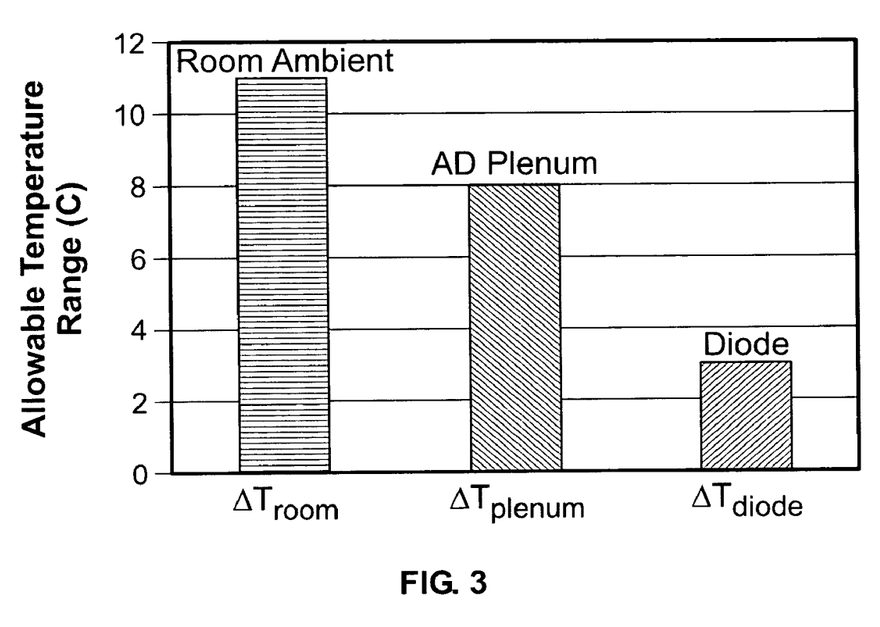
FIG. 3 illustrates the allowable temperature variations for the CT system illustrated in FIGS. 1 and 2.
Figure 4:
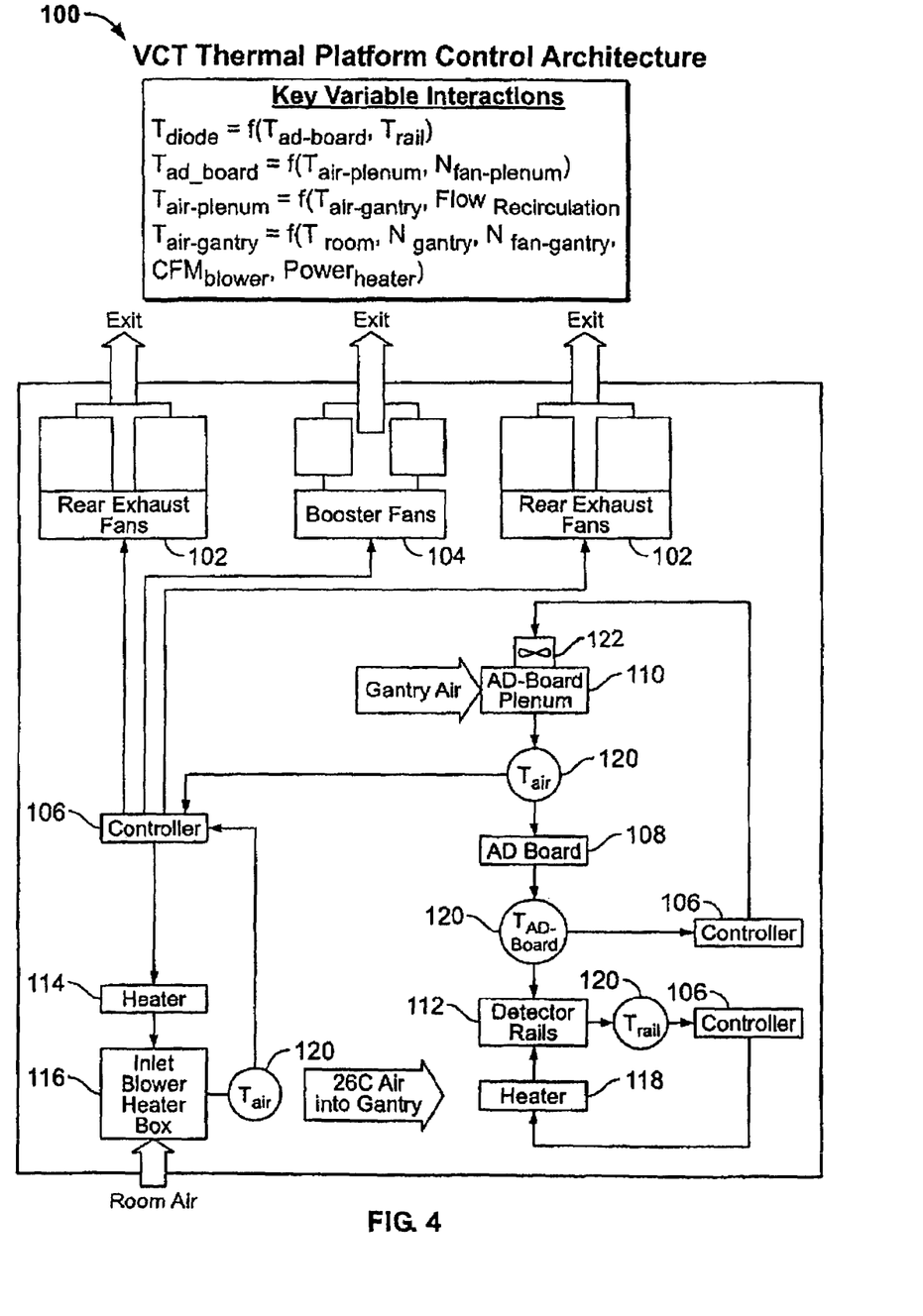
FIG. 4 illustrates a system level thermal control system.

FIG. 3 illustrates the allowable temperature variations for the CT system illustrated in FIGS. 1 and 2. FIG. 4 illustrates one thermal control system 100 useable with the system illustrated in FIGS. 1 and 2 and other CT systems and Volume CT systems (VCT). System 100 includes a plurality of rear exhaust fans 102 and a plurality of booster fans 104. Although illustrated with a particular number of fans, it is contemplated that the benefits of the invention accrue to systems with various fans including a single exhaust fan or a single booster fan. System 100 also includes at least one controller 106. An analog to digital board (AD Board) 108 is situated in an AD Board plenum 110 and operationally coupled to a detector rail(s) 112. One controller 106 controls a heater 114 positioned in an inlet blower heater box 116. A heater 118 may be positioned in a flow path with detector rails 112 and controlled by controller 106. As illustrated in the figures and as described below a plurality of temperature sensors 120 are situated in various places.

The herein described methods and apparatus provide, in one embodiment, for an integrated thermal system design which uses variable speed fans with PID (Proportional, Integral, Derivative) feedback control for both local diode temperature control and global system level air temperature and flow control. The local variable speed temperature control system uses the temperature of the digital modules and temperature control of the detector rail to maintain substantially optimal diode temperature control such as is described in co-pending application Ser. No. 10/710,213, filed Jun. 25, 2004, titled Variable Speed Fans for Advanced DAS/Detector Thermal Management, and is hereby incorporated in its entirety. The global thermal control system includes an inlet air blower with heaters used to provide controlled air into the front side of the CT system for consumption by the local digital module control system. Further, the inlet blower heater system provides controlled airflow to provide continuous air mixing. By providing inlet air to the front side of the gantry and the air mixing, the effects of air recirculation from the exhaust of the electronics and tube heat exchanger are minimized. The continuous flow also prevent local pockets of hot air to be trapped and mixing when gantry rotation begins thus preventing temperature spikes during scanning. One effect of the global thermal control system is to reduce the variation in air temperature that is seen by the local digital module temperature control system. FIG. 3 illustrates how the room the temperature control ranges vary from room ambient down to the photo diode of the detector. As can be seen the room ambient graph has the largest temperature range which the global control system reduces to a level that the local system can compensate for to ultimately control the photo diode down to a very narrow range as required for proper performance. A further feature of the herein described methods and apparatus provide substantially optimized audible noise and fan reliability both of which increase with fan speed.

Thus, by using a variable speed plenum fan 122 at the local level, a wider range of inlet air temperatures can be accommodated by modifying air velocity to compensate for temperature difference between cooling air and target electronic components. Similarly, by using variable speed gantry exhaust fans, both a wide variation in room ambient air and gantry rotational speeds can be accommodated. Therefore, by using the inlet air temperature of local temperature control system as feedback to control the gantry exhaust fans the overall system audible noise and fan reliability can be substantially optimized as there will be multiple design points that satisfy the room ambient, system power output, and gantry rotational speed.

The following equations illustrate relationships.

$$T_{plenum\text{-}inlet} = f(Q_{AD\text{-}Boards}, Q_{xray\text{-}tube}, N_{gantry}, T_{ambient}, Q_{inlet\text{-}blower}, N_{gantry\text{-}fans}) \quad (eq\ 1)$$

illustrates that the temperature at the plenum inlet ($T_{plenum\text{-}inlet}$) is a function (f) of heat (Q) produced at the AD-board(s), the x-ray tube, and the inlet blower, the rotation speed of the gantry ($N_{gantry}$), the number (N) of gantry fans, and the ambient temperature ($T_{ambient}$).

$$T_{AD} = f(N_{plenum\text{-}fans}, T_{plenum\text{-}inlet}) \quad (eq\ 2)$$

illustrates that the temperature at the AD board(s) and/or AD plenum is a function of the plenum inlet temperature and the number of plenum fans.

$$DB_{system\text{-}fan} = f(N_{plenum\text{-}fans}, N_{gantry\text{-}fans}) \quad (eq\ 3)$$

illustrates that total noise (DB, decibels) is a function of the number of plenum fans and gantry fans.

$$Life_{plenum\text{-}fans} = f(N_{plenum\text{-}fans}, T_{plenum\text{-}inlet}) \quad (eq\ 4)$$

illustrates factors (number of fans and temperature at plenum inlet) that affect plenum fan replacement times.

$$Life_{gantry\text{-}fans} = f(N_{gantry\text{-}fan}, T_{gantry\text{-}exhaust}) \quad (eq\ 5)$$

illustrates factors (number of fans and temperature at gantry exhaust) that affect gantry fan replacement times.

Based on nearly constant electronic power output and the typically low air temperatures encountered in a CT system eq1, 4 and 5 can be simplified to the following.

$$T_{plenum\text{-}inlet} = f(Q_{xray\text{-}tube}, N_{gantry}, T_{ambient}, N_{gantry\text{-}fans}) \quad (eq\ 1a)$$

$$Life_{plenum\text{-}fans} = f(N_{plenum\text{-}fans}) \quad (eq\ 4a)$$

$$Life_{gantry\text{-}fans} = f(N_{gantry\text{-}fans}) \quad (eq\ 5a)$$

Thus, based on the allowable inlet plenum air temperatures that can be accommodated by the local control system variable speed fans, there are multiple possible gantry fan speeds that will give an acceptable AD board temperature to provide the desired diode temperature. This means that the gantry and fan speeds if tied together in a common control system can be optimized or substantially optimized to provide substantially minimum noise and substantially maximum life for any combination of room ambient and x-ray tube output power.

Figure 5:
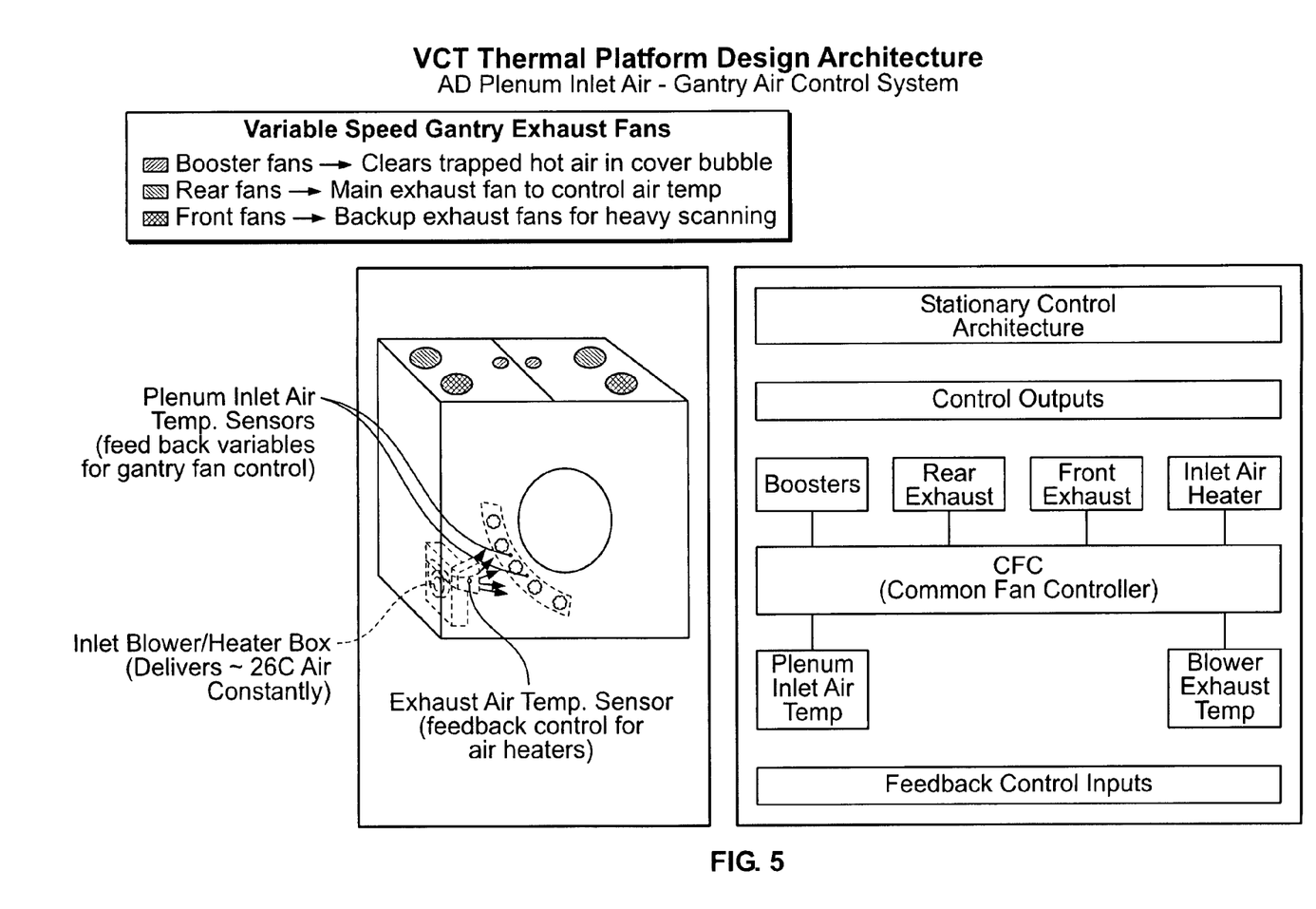
FIG. 5 illustrates a system level thermal control system.
Figure 6:
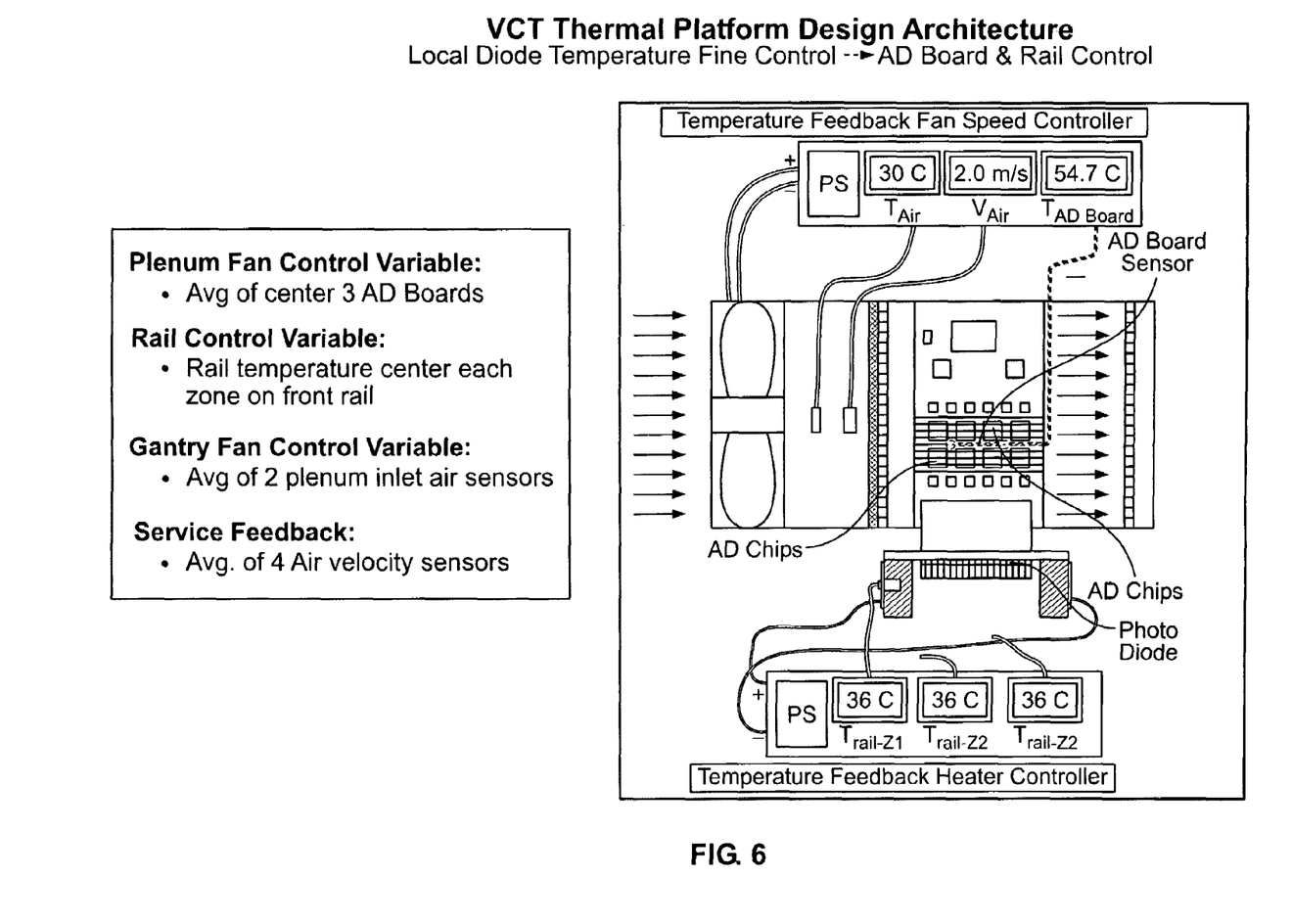
FIG. 6 illustrates a system level thermal control system.

In one embodiment, the gantry exhaust fans are tied to a PID feedback controller that uses the inlet plenum air temperature as the PID controllers feed back variable. Further, the gantry exhaust fans are broken into banks of fans that can be controlled to run at different speeds to achieve optimal performance. One design of a system level control system is illustrated in FIGS. 4, 5, and 6. One embodiment is as illustrated in all of FIGS. 4, 5, and 6, while other embodiments utilize just some of the features illustrated in some of FIGS. 4, 5, and 6.

A further feature of the herein described methods and apparatus are the service feedback mechanisms built into the design. Below is a list of the service features enabled by the herein described system level control architecture:

1. Air filter maintenance—The air flow after each air filter is monitored via a velocity sensor (a pressure sensor system can also be used) to send out a message to a service or a user that at least one air filter is critically clogged and need to be cleaned. This will enable pre-emptive maintenance before the filters have clogged to the point of causing system performance degradation.

2. Redundant sensor error handling—Multiple sensors and error trapping are employed to detect a bad sensor and remove it from the feedback loop. By using multiple sensors, an average value can be used for temperature and flow sensing feedback (e.g., as illustrated in FIG. 6). When one of the controllers detects a bad sensor the control software removes the sensor from the averaging scheme and sends an error message to field service to replace the sensor at the next available scheduled down time. When any feedback system is down to only 2 working sensors to average a request for immediate service is sent out.

3. Imminent fan failure—The control systems continually monitor for change in current required to run the fans at a given speed compared to baseline current draw (when fans where new). Once a certain level of degradation is seen (e.g., a rise in current required by a fan) an error message is sent to the system warning that a fan is failing and needs to be replaced at the next opportunity.

Technical effects of the herein described methods and apparatus include a more precise local control while maintaining low audible noise. A further technical effect of an integrated system is the ability to provide preemptive field service data to minimize unscheduled maintenance and eliminate the need for fixed PM schedules. And another technical effect is the ability to optimize against audible noise and fan life to achieve a more robust CT system design.

Additional methods and apparatus incorporate a system level variable speed fan temperature control system that is tied to the local electronic cooling air temperature. Such a system allows the temperature within a gantry to vary without degrading system performance. A substantially minimization in air recirculation via forced controlled inlet airflow at the front of the gantry is therefore enabled. And a pre-heating of the inlet air enables a reduced sensitivity to low room ambient conditions. In one embodiment, multiple banks of gantry fans phased to provide minimal audible noise and maximum fan life via optimized fan speed set points. In some embodiments, smart service algorithms eliminate the need for fixed maintenance schedules for air filter cleaning or fan replacement, smart service algorithms warn of impending performance degradation due to dirty air filters or imminent fan failure, and/or smart control algorithms that take advantage of multiple redundant sensors that allow for continued operation in the event of a sensor failure.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method of cooling a medical imaging system that includes a gantry comprising;
    supplying air to the gantry;
    conditioning the supplied air to maintain a predetermined bulk temperature and to facilitate reducing the variation of temperature within the gantry;
    independently channeling a variable amount of the conditioned air to a plurality of heat producing electronic devices, wherein the heat producing electronic devices are coupled in flow communication with a plurality of fans, wherein at least one of the heat producing electronic devices is coupled within a plenum, wherein at least one of the fans is a plenum fan coupled at an inlet of the plenum coupled within the gantry, and wherein at least one of the fans is an exhaust fan orientated to exhaust the supplied air outside of the gantry;
    operating a first one of the fans at a speed different than a second one of the fans;
    detecting local temperatures at at least the heat producing electronic devices and the plenum; and
    controlling the plenum fan and the exhaust fan based on at least one of the detected local temperatures, the at least one of the detected local temperatures used as a feedback variable to control at least the exhaust fan.

2. A method in accordance with claim 1 further comprising varying the speeds of the fans to facilitate conditioning the supplied air at a plurality of locations within the gantry.

3. A method in accordance with claim 2 wherein the plurality of fans operate independently.

4. A method in accordance with claim 1 wherein conditioning the supplied air to maintain a predetermined bulk temperature further comprises:
    receiving a first signal indicative of a bulk temperature in the gantry;
    comparing the bulk temperature signal to a predetermined selectable threshold; and
    controlling the flow of supplied air to the gantry using the comparison.

5. A method in accordance with claim 1 wherein conditioning the supplied air comprises heating the supplied air to a predetermined selectable threshold.

6. A method in accordance with claim 1 wherein conditioning the supplied air further comprises:
    receiving a signal indicative of a local temperature of at least one of a plurality of locations within the gantry;
    comparing the signal to a predetermined selectable threshold;
    controlling the flow of air to the at least one of the plurality of locations using the comparison.

7. A method in accordance with claim 1 wherein conditioning the supplied air further comprises conditioning the flow of the supplied air channeled to at least one detector rail.

8. A method in accordance with claim 7 further comprising:
    receiving a signal indicative of a local temperature at the at least one detector rail;
    comparing the signal to a predetermined selectable threshold;
    controlling a heater using the comparison to facilitate maintaining a substantially constant temperature of the at least one detector rail.

9. A method in accordance with claim 1 wherein supplying air to the gantry further comprises channeling room air using an inlet heater blower box.

10. A method in accordance with claim 1 further comprising exhausting the supplied air using the exhaust fan.

11. A medical imaging system comprising:
    a gantry including a controller configured to receive a plurality of signals indicative of temperatures at a plurality of respective locations within said gantry;
    a local thermal control system configured to maintain a predetermined temperature of a plurality of heat producing electronic devices within said gantry, wherein at least one of said heat producing electronic devices is coupled within a plenum, wherein said local thermal control system further comprises a plurality of fans coupled in flow communication with said heat producing electronic devices, wherein at least one of the fans is a plenum fan coupled at an inlet of the plenum coupled within said gantry, wherein a first one of said fans operating at a speed different than a second one of said fans, wherein said local thermal control system further comprises a plurality of temperature sensors configured to detect local temperatures at said heat producing electronic devices and said plenum; and
    a bulk thermal control system configured to maintain a predetermined temperature within said gantry to facilitate reducing the variation of temperature within said gantry, wherein said bulk thermal control system comprises at least one exhaust fan coupled to said gantry and orientated to exhaust the supplied air outside of said gantry, wherein said bulk thermal control system and said local thermal control system are communicatively coupled to said controller, said controller configured to control said exhaust fan and said plenum fan based on at least one of said detected local temperatures, said controller configured to use said at least one of said detected local temperatures as a feedback variable to control at least said exhaust fan.

12. A medical imaging system in accordance with claim 11 wherein said gantry further comprises a plenum to circulate air in said gantry.

13. A medical imaging system in accordance with claim 11 wherein said heat producing electronic devices are configured to transmit a signal indicative of said at least one detected local temperatures to said controller, said controller controlling said fans to maintain a local temperature of a respective heat producing electronic device at a substantially constant temperature.

14. A medical imaging system in accordance with claim 11 wherein said heat producing electronic devices includes at least one detector rail.

15. A medical imaging system in accordance with claim 14 wherein said local thermal control system further comprises a heater communicatively coupled to said controller and in a flow path with said at least one detector rail, said heater receiving signals from said controller and maintaining the heat of air in a flow path with said at least one detector rail.

16. A medical imaging system in accordance with claim 11 wherein said bulk thermal control system further comprises an inlet heater blower box in a flow path with said gantry and communicatively coupled to said controller such that said controller controls the output of air from said inlet heater blower box to said gantry.

17. A medical imaging system in accordance with claim 16 wherein said bulk thermal control system further comprises a heater in a flow path with said inlet heater blower box and communicatively coupled to said controller such that said controller maintains the heat of air input into said inlet heater blower box.

18. A medical imaging system in accordance with claim 11 wherein said bulk thermal control system further comprises at least one rear exhaust fan and at least one booster fan to selectively exhaust air from said gantry.

19. A medical imaging system in accordance with claim 11 wherein said bulk thermal control system further comprises at least one front exhaust fan to selectively exhaust air from said gantry.

20. A medical imaging system in accordance with claim 11 wherein the first one of said fans operating at a non-zero speed different than a non-zero-speed of the second one of said fans.

* * * * *